United States Patent
Gormsen et al.

[11] Patent Number: 5,929,017
[45] Date of Patent: Jul. 27, 1999

[54] ENZYMATIC DETERGENT COMPOSITION

[75] Inventors: Erik Gormsen, Virum, Denmark;
Naoko Ikegami, Tokyo, Japan;
Masanobu Abo, Chiba-ken, Japan;
Shinobu Takagi, Chiba-ken, Japan;
Noriko Tsutsumi, Chiba-ken, Japan;
Torben Halkier, Birkerød, Denmark

[73] Assignee: Novonordisk A/S, Bagsvaerd, Denmark

[21] Appl. No.: 08/809,440

[22] PCT Filed: Oct. 26, 1995

[86] PCT No.: PCT/DK95/00424

§ 371 Date: Apr. 24, 1997

§ 102(e) Date: Apr. 24, 1997

[87] PCT Pub. No.: WO96/13578

PCT Pub. Date: May 9, 1996

[30] Foreign Application Priority Data

Oct. 26, 1994 [DK] Denmark ................................. 1236/94
Jul. 14, 1995 [DK] Denmark ................................. 0828/95

[51] Int. Cl.$^6$ .................................................. C11D 3/386
[52] U.S. Cl. .......................... 510/392; 510/530; 510/320; 510/305; 510/306; 435/198; 435/912
[58] Field of Search ..................... 510/530, 392, 510/393, 320, 305, 306; 435/198, 912

[56] References Cited

U.S. PATENT DOCUMENTS 3,634,195  1/1972  Melachouris .............................. 195/66

FOREIGN PATENT DOCUMENTS

| 0238023 A2 | 9/1987 | European Pat. Off. . |
| 0385401 | 9/1990 | European Pat. Off. . |
| 0489718 A1 | 6/1992 | European Pat. Off. . |
| WO 8700859 A1 | 2/1987 | WIPO . |
| WO 9401541 A1 | 1/1994 | WIPO . |
| 94/14940 | 7/1994 | WIPO . |
| WO 9414940 A1 | 7/1994 | WIPO . |
| 96/13578 | 5/1996 | WIPO . |
| 97/27276 | 7/1997 | WIPO . |

OTHER PUBLICATIONS

Chemical Abstracts: 95:111511y "Lipolytic Activity of Thermophilic Fungi of Paddy Straw Compost", 1981.
EMBL, Genbank, DDBJ, Accession No. A34959.
Satyanarayana, T., et al., Chemical Abstracts, vol. 95, No. 13, pp. 344 (1981) Abstract No. 111511y.
Dialog Information Services, file 351, Derwent WPI, Dialog accession No. 008384112, WPI accession No. 90–271113/36.
Koritala, S., et al., JAOCS, vol. 64, No. 4, pp. 509–513, (1987).
Aisaka, K., et al., Agric. Biol. Chem., vol. 43, No. 10, pp. 2125–2129 (1979).
Schipper, M.A.A., Persoonia, vol. 14, Part 2, pp. 133–148, (1990).

*Primary Examiner*—Kery Fries
*Attorney, Agent, or Firm*—Steve T. Zelson, Esq.; Valeta Gregg, Esq.

[57] ABSTRACT

A lipolytic enzyme with high activity at alkaline pH in the absence of $Ca^{++}$ can be obtained from strains of filamentous fungi belonging to the genus Absidia. The lipolytic enzymes are effective for improving the effect of detergents towards fatty soiling.

31 Claims, 5 Drawing Sheets pH profile of A. *blakesleeana* NN000591 lipase pH profile of A. corymbifera NN100062 lipase pH profile of A. reflexa NN102424 lipase

ENZYMATIC DETERGENT COMPOSITION

CROSS-REFERENCE TO RELATED APPLICATIONS

This application is a 35 U.S.C. 371 national application of PCT/DK95/00424 filed Oct. 26, 1995 and claims priority under 35 U.S.C. 119 of Danish applications 1236/94 filed Oct. 26, 1994 and 0828/95 filed Jul. 14, 1995, the contents of which are fully incorporated herein by reference.

TECHNICAL FIELD

This invention relates to an enzymatic detergent composition and an enzymatic detergent additive comprising a lipolytic enzyme.

BACKGROUND ART

Lipolytic enzymes are known to be useful in detergents to improve the removal of fatty stains. Thus, in recent years Lipolase®, a microbial lipase derived from the fungus *Thermomyces lanuginosus* (also called *Humicola lanuginosa*), has been introduced into many commercial brands of detergent.

Other microbial lipases have also been suggested for use in detergents, e.g. bacterial lipase from *Pseudomonas cepacia* (U.S. Pat. No. 4,876,024), from Streptomycetes (WO 94/14940) and from *Gongronella butleri* strain NRRL 3521 (U.S. Pat. No. 3,634,195, the strain was previously named *Absidia butleri*, see K. H. Domsch et al., *Compendium of Soil Fungi*, Academic Press 1980, p. 381).

Many detergents are alkaline with a high pH in solution (e.g. around pH 10) and contain a builder to bind $Ca^{++}$ ions, so there is a need for lipolytic enzymes with high activity at high pH in the absence of $Ca^{++}$.

SUMMARY OF THE INVENTION

Surprisingly, we have found that a lipolytic enzyme with high activity at alkaline pH in the absence of $Ca^{++}$ can be obtained from strains of filamentous fungi belonging to the genus Absidia and that the lipolytic enzymes are effective for improving the effect of detergents.

Accordingly, the invention provides an enzymatic detergent composition comprising a surfactant and an alkaline Absidia lipolytic enzyme. The invention also provides a method for removing fatty soiling from textile, comprising washing the textile in an aqueous solution comprising the detergent composition.

The invention further provides an enzymatic detergent additive containing an Absidia lipolytic enzyme as an active component, provided in the form of a non-dusting granulate, a stabilized liquid, a slurry, or a protected enzyme.

Another aspect of the invention provides a lipolytic enzyme which is derived from a strain of *Absidia reflexa* and has a higher lipolytic enzyme activity at pH 10 than at pH 9 in the absence of $Ca^{++}$.

U.S. Pat. No. 3,634,195 describes production of lipase from *A. cylindrospora* var. *rhizomorpha* NRRL 2815 and *A. blakesleeana* NRRL 1305. S. Koritala et al., *J. Am. Oil Chem. Soc.*, 64 (4), 509–13 (1987) discloses that soybean oil was partially hydrolyzed when incubated with *A. coerula* NRRL 5926 and *A. ramosa* NRRL 1309. T. Satyanarayana, *Current Science*, 50 (15), 680–2 (1981) discloses the secretion of lipase by a strain of *A. corymbifera*. K. Aisaka et al., *Agric. Biol. Chem.*, 43 (10), 2125–2129 (1979) describes the formation of a lipoprotein lipase from *Absidia hyalospora* strain KY 303 (now classified as *A. blakesleeana*).

However, the prior art does not disclose or suggest that lipolytic enzymes from Absidia are active at high pH in the absence of $Ca^{++}$, nor that they are useful in detergents.

DETAILED DISCLOSURE OF THE INVENTION

Microorganisms

Figure 1:
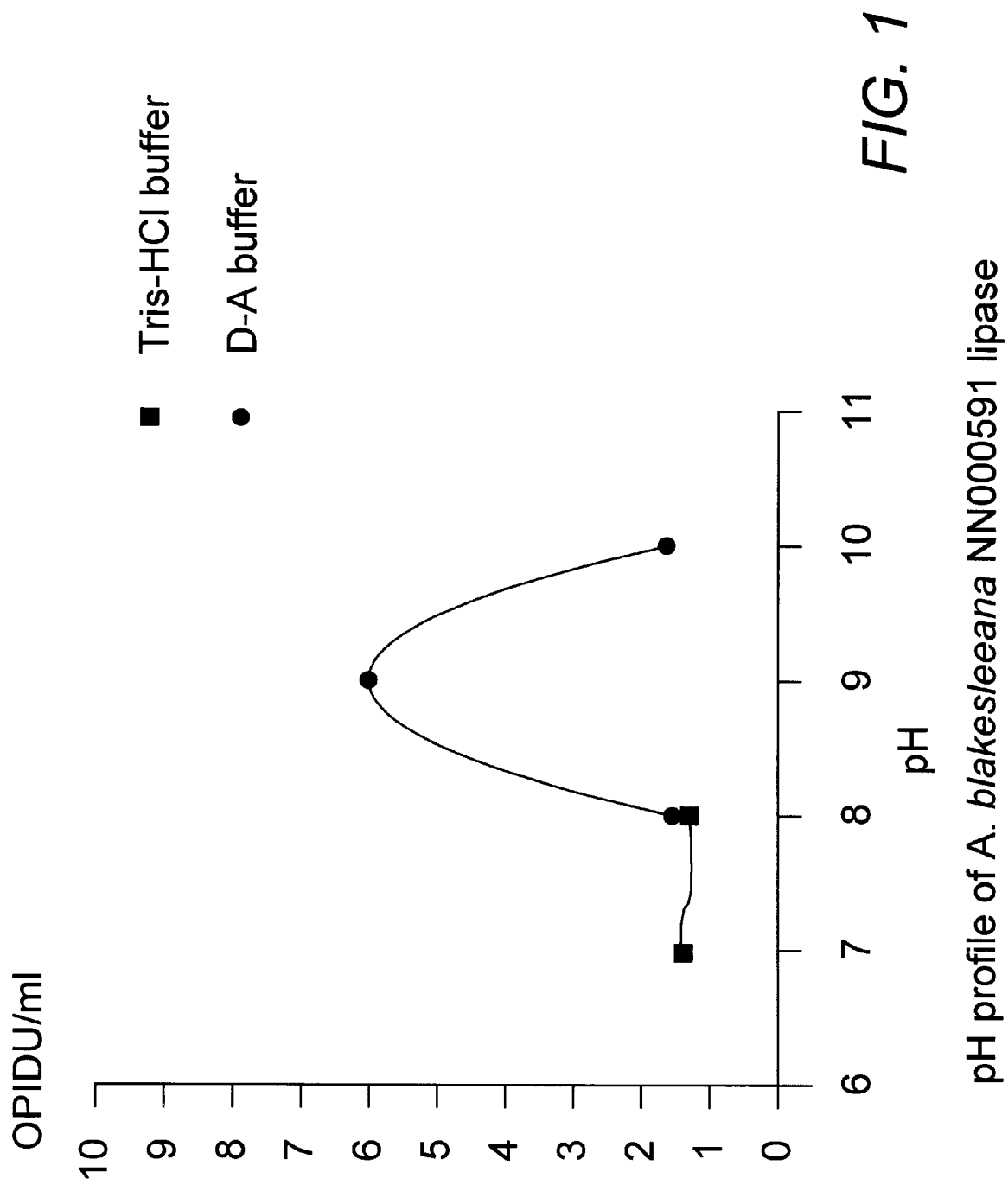
FIGS. 1–5 show graphs of lipolytic enzyme activity versus pH in the absence of $Ca^{++}$ for some purified lipolytic enzymes according to the invention. Details are given in Example 8.
Figure 2:
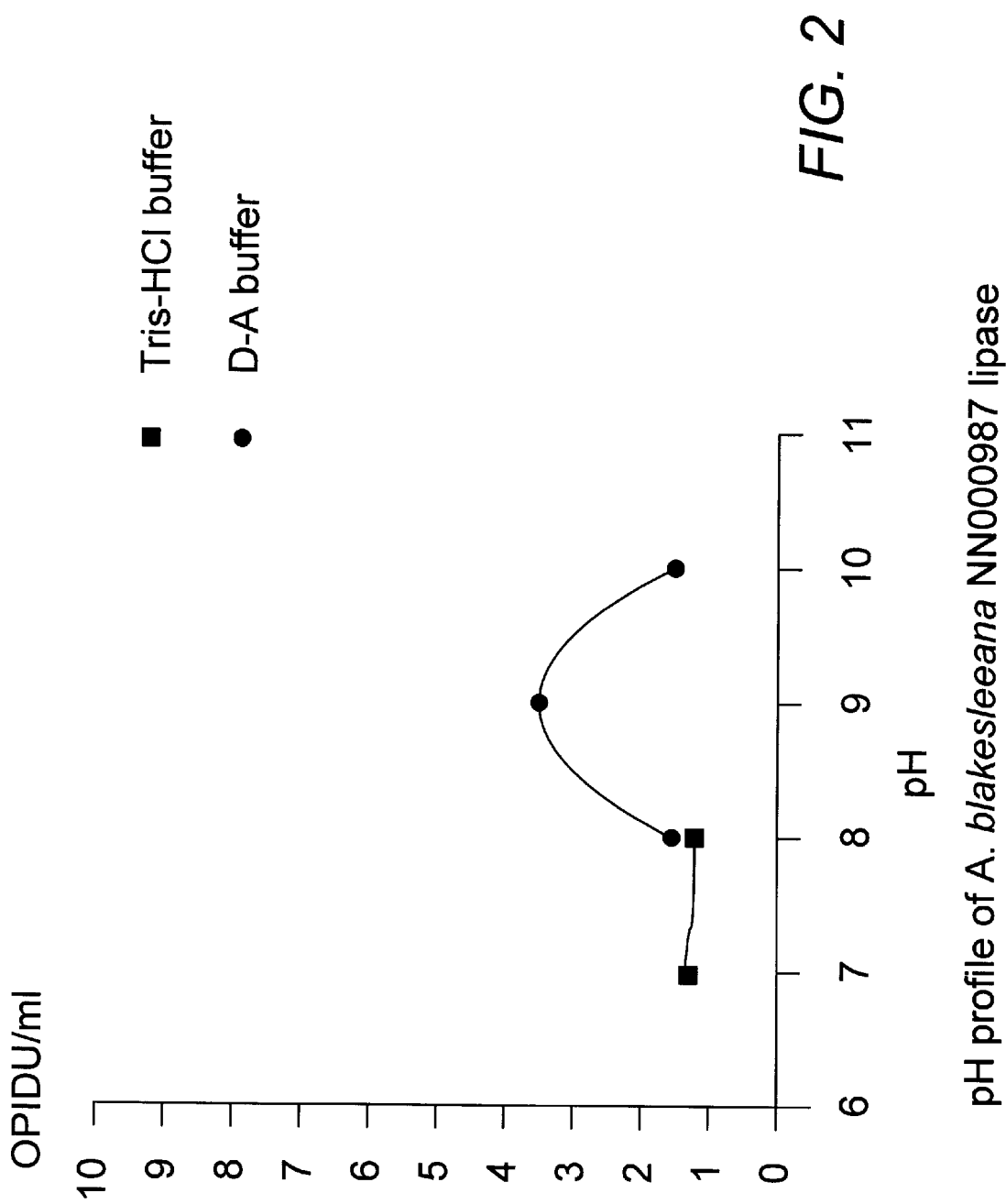
Figure 3:
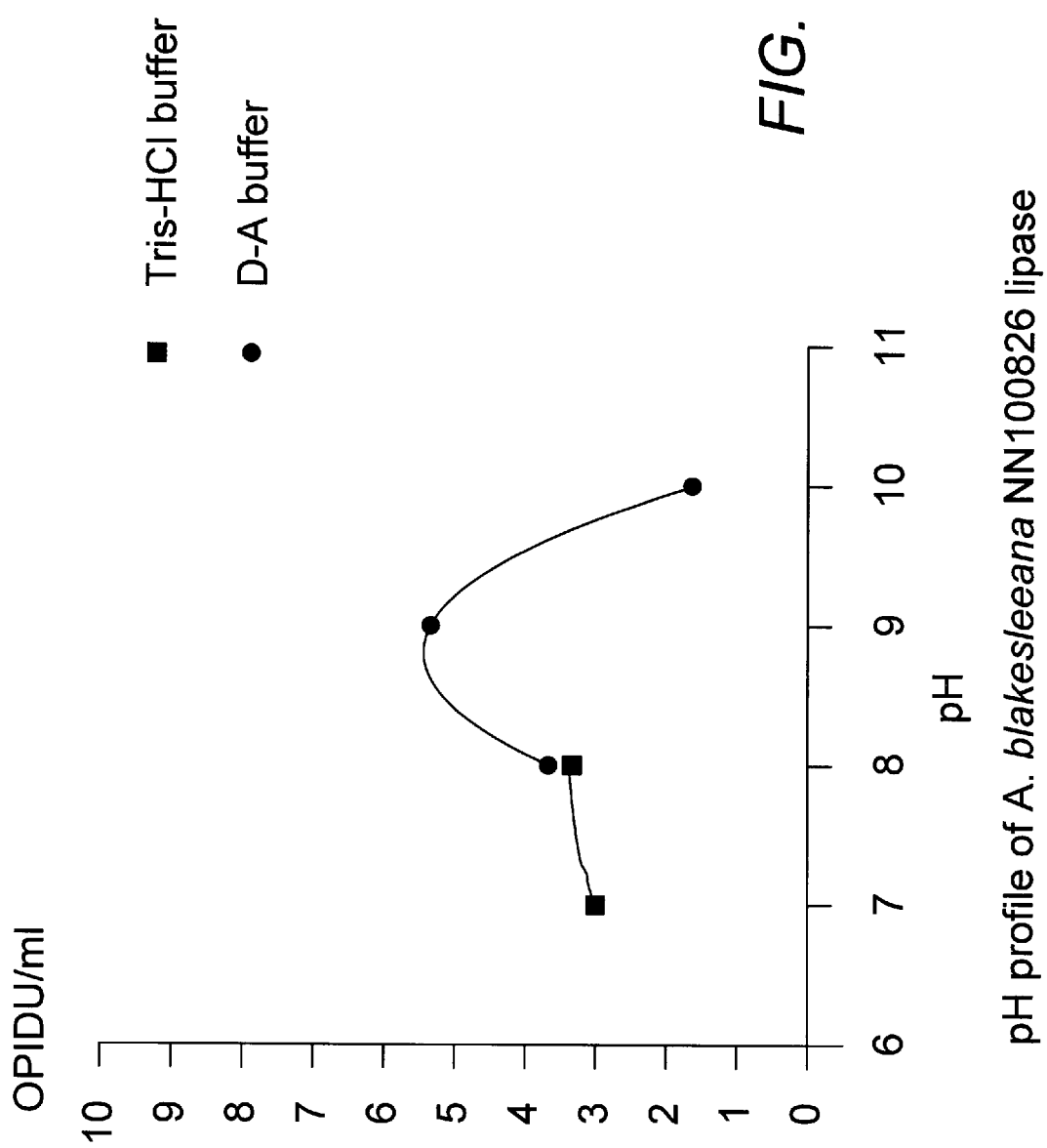
Figure 4:
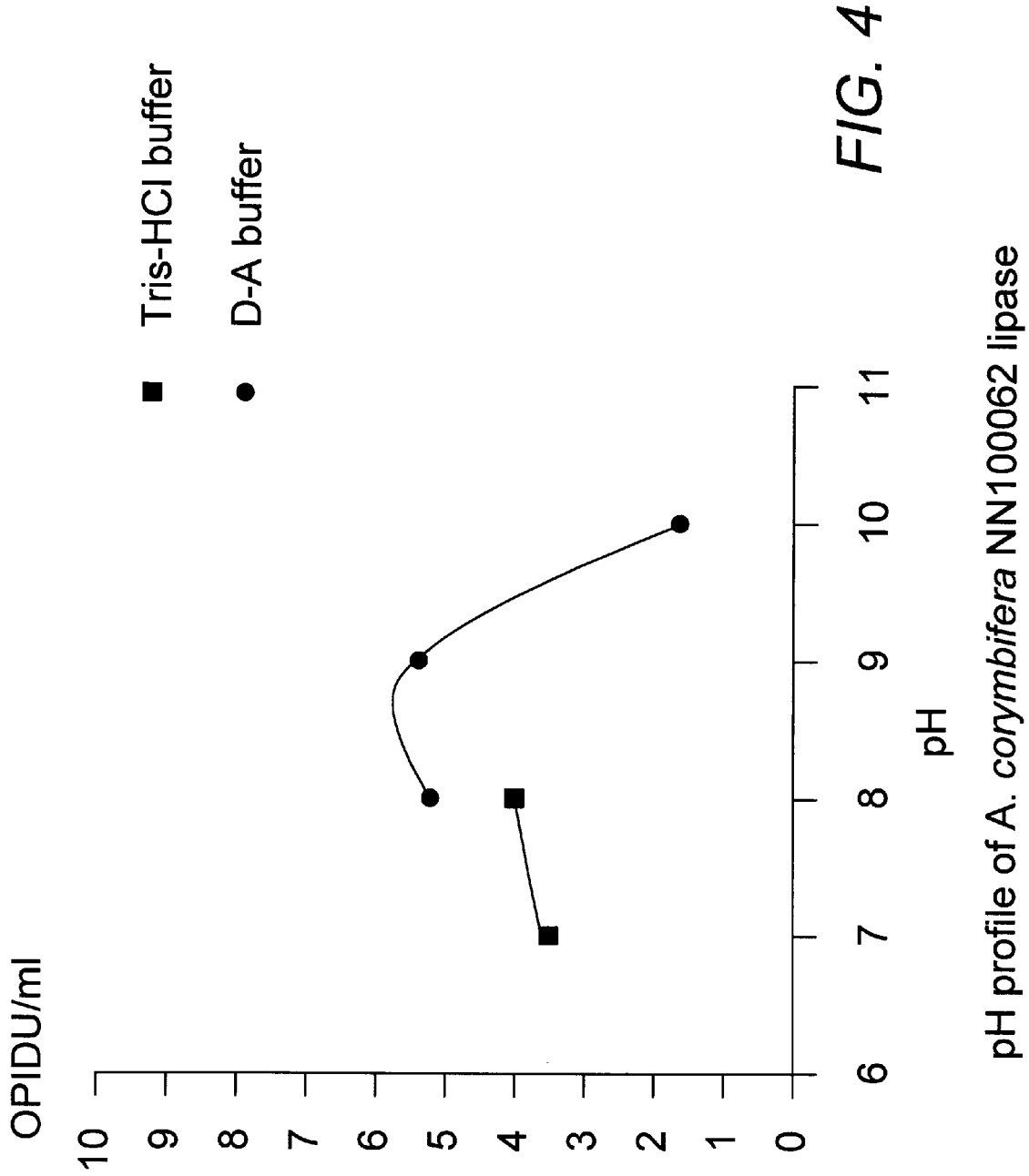
Figure 5:
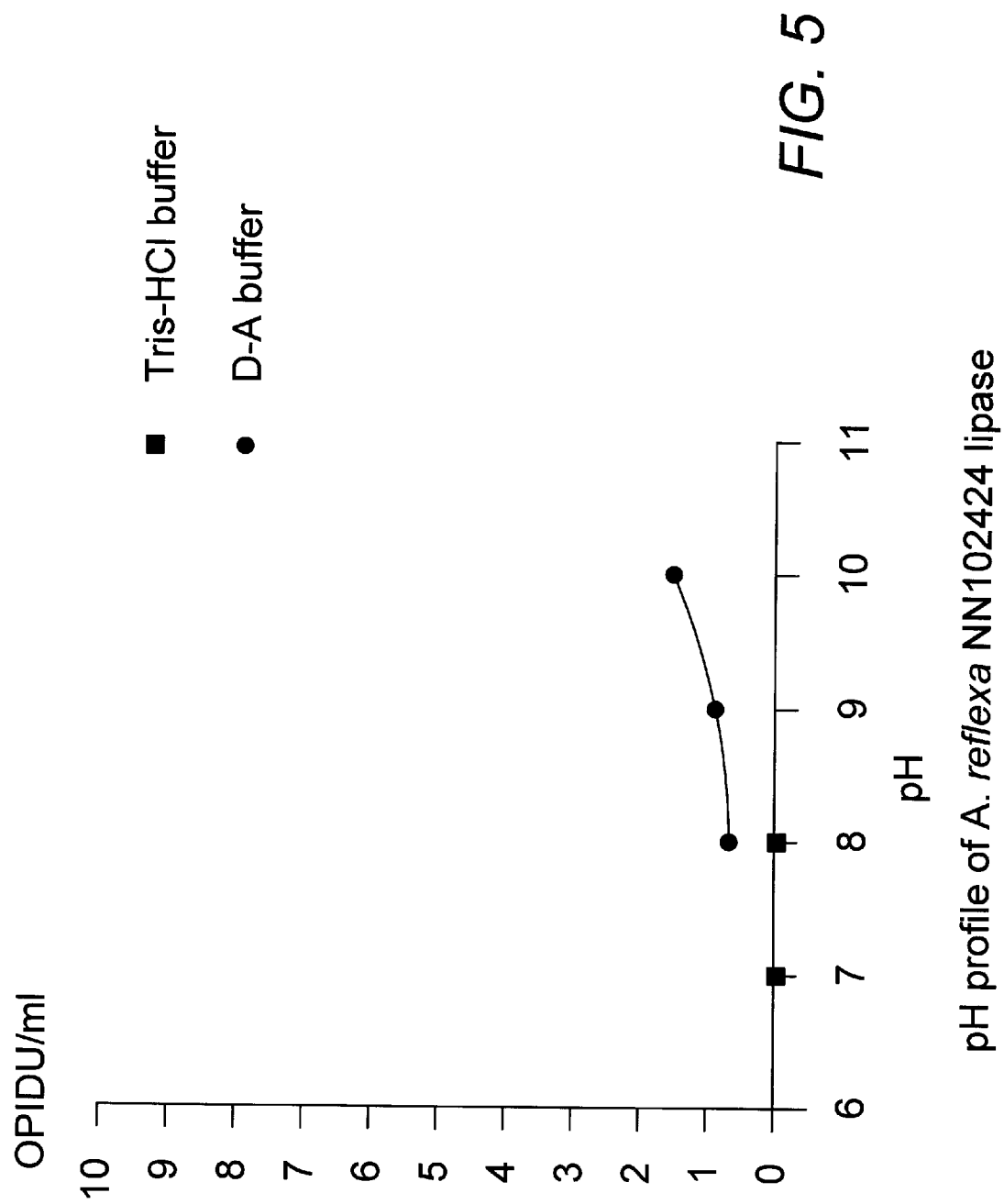

The microbial strain used in this invention belongs to the genus Absidia, as described in M. A. A. Schipper, *Persoonia*, Vol. 14, Part 2, pp. 133–148 (1990). Within this genus, the following subgenera, groups, species and strains are preferred. Variants and mutants thereof capable of producing lipolytic enzyme may also be used in the invention. It is noted that a number of previously recognized species names were reclassified by Schipper, Op. cit., and for convenience the previously used names of some strains are also listed below.

The prior art does not describe lipolytic enzyme production from *A. reflexa*, a species which was not classified by Schipper. The production of a lipolytic enzyme by this species has not previously been described, and we have found that the lipolytic enzymes from this species is distinct from the lipolytic enzymes from the subgenera Mycocladus and Absidia.

| Subgenus, group | Species name | Previous species name | Inventors' strain No. | Deposit number(s) |
|---|---|---|---|---|
| Subgenus Mycocladus | A. blakesleeana | A. blakesleeana | NN100826 | NRRL 1304 ATCC 10148a CBS 100.28 CMI 111736 |
| | | A. blakesleeana | NN102406 | CBS 100.36 |
| | | A. blakesleeana | NN102407 | CBS 102.36 NRRL 2696 |
| | | A. blakesleeana | NN102408 | CBS 420.70 |
| | | A. blakesleeana | NN102413 | NRRL 1305 |
| | | A. griseola | NN000987 | ATCC 20430 |
| | | A. griseola | NN102403 | CBS 519.71 ATCC 22618 IFO 9472 |
| | | A. griseola var. iguchii | NN000591 | ATCC 20431 |
| | | A. hyalospora | NN102432 | CBS 173.67 NRRL 2916 |
| | A. blakesleeana var. atrospora | A. atrospora | NN102423 | CBS 518.71 ATCC 22617 IFO 9471 |
| | A. corymbifera | A. corymbifera | NN100060 | CBS 100.31 IFO 4009 NRRL 2982 |
| | | A. corymbifera | NN100062 | IFO 8084 |
| | | A. corymbifera | NN102404 | CBS 102.48 |
| | | A. corymbifera | NN102405 | CBS 582.65 ATCC 22574 NRRL 1309 |
| | | A. hesseltinii | NN102426 | CBS 958.68 ATCC 24263 |

-continued

| Subgenus, group | Species name | Previous species name | Inventors' strain No. | Deposit number(s) |
|---|---|---|---|---|
| Subgenus Absidia Group B | A. cylindrospora var. rhizomorpha | — | NN102422 | CBS 154.63 NRRL 2815 |
|  | A. pseudocylindro spora | — | NN102434 | ATCC 24169 CBS 100.62 NRRL 2770 |
| — | A. reflexa | — | NN102424 | ATCC 44896 IFO 5874 |
| — | A. sporophora-variabilis | — | NN102427 | ATCC 36019 |

The above-mentioned strains are freely available from the following depositary institutions for microorganisms. Multiple numbers in the same box indicate multiple deposits of the same strain.

NRRL: Agricultural Research Service Culture Collection, 1815 North University Street, Peoria, Ill. 61604, USA.

ATCC: American Type Culture Collection, 12301 Parklawn Drive, Rockville, Md. 20852, USA.

CBS: Centraal Bureau voor Schimmelcultures, Oosterstraat 1, 3740 AG Baarn, Netherlands.

CMI: CAB International Mycological Institute, Ferry Lane, Kew, Surrey TW9 2AF, U.K.

IFO: Institute for Fermentation, 17-85 Juso-honmachi 2-chome, Yodogawa-ku, Osaka 532, Japan.

Lipolytic enzyme may be produced by cultivating any of the above microorganisms in a suitable nutrient medium, optionally followed by recovery and purification, according to methods well known in the art or as described in the examples of this specification.

Enzyme Properties

The enzymes of this invention are lipolytic enzymes. In the present context the term "lipolytic enzyme" is intended to indicate an enzyme classified under the Enzyme Classification number E.C. 3.1.1.—(Carboxylic Ester Hydrolases) in accordance with the Recommendations (1992) of the International Union of Biochemistry and Molecular Biology (IUBMB). Lipolytic enzymes thus exhibit hydrolytic activity towards at least one of the types of ester bonds mentioned in the context of E.C. 3.1.1, e.g. ester bonds present in mono-, di- and triglycerides, phospholipids (all classes), thioesters, cholesterol esters, wax-esters, cutin, suberin, synthetic esters, etc. As an example, the lipolytic enzymes of the invention may have activity towards triglycerides (lipase activity, E.C. 3.1.1.3), e.g. 1,3-positionally specific lipase activity.

The lipolytic enzymes of this invention are characterized by having a high activity at alkaline pH (about pH 9–10), even in the absence of free $Ca^{++}$.

More specifically, these lipolytic enzymes have optimum activity at about pH 9 or higher (have a higher activity at pH 9 than at pH 8) when tested in the absence of free $Ca^{++}$ by the OPID method described below.

Some preferred lipolytic enzymes have an activity of at least 3 OPID units/ml when tested at pH 9 without free $Ca^{++}$ and a lipolytic enzyme concentration of 20 LU/ml (LU and OPID are lipolytic enzyme activity units defined below), i.e. a ratio between activities on olive oil and tributyrin of at least 0.15 OPID/LU. Such lipolytic enzymes can be derived from strains of Absidia subgenus Mycocladus, e.g. the species and strains listed above.

Another group of preferred lipolytic enzymes have a higher lipolytic enzyme activity at pH 10 than pH 9 in the absence of $Ca^{++}$. Such a lipolytic enzyme can be derived from A. reflexa, e.g. the strain listed above. This lipolytic enzyme is novel and is provided by the invention.

Lipase Activity Determination (LU)

One Lipase Unit (LU) is the amount of enzyme which liberates 1 mmol of titratable fatty acid per minute with tributyrin as substrate and gum arabic as emulsifier at 30.0° C., pH 7.0 (phosphate buffer).

Lipase Activity Determination (OPID)

The lipolytic enzyme activity without free $Ca^{++}$ in the range pH 7–10 is tested with a substrate emulsion of olive oil: 2% PVA solution (1:3)at 40° C. for 10 minutes, at a specified pH. At the end of the reaction, the reaction mixture is extracted by chloroform: methanol (1:1) at acidic conditions, and the fatty acid released during the reaction is measured by TLC-FID analysis (Iatroscan). One unit (OPIDU) is taken as the release of a mmole of fatty acid per minute.

In each test, 1.0 mM EDTA is used together with 200 mM of buffer (Tris-HCl buffer at pH 7 and 8, diethanol amine buffer at pH 8, 9 and 10).

Immunochemical Properties

Positionally non-specific lipolytic enzymes having immunochemical properties identical or partially identical to those of a lipolytic enzyme native to a strain of Absidia and having the stated properties are within the scope of the invention.

The immunochemical properties can be determined by immunological cross-reaction identity tests. The identity tests can be performed by the well-known Ouchterlony double immunodiffusion procedure or by tandem crossed immunoelectrophoresis according to I. M. Roitt; Immunology, Gower Medical Publishing (1985) and N. H. Axelsen; Handbook of Immunoprecipitation-in-Gel Techniques, Blackwell Scientific Publications (1983), Chapters 5 and 14. The terms immunochemical identity (antigenic identity) and partial immunochemical identity (partial antigenic identity) are described in Axelsen, supra, Chapters 5, 19 and 20 and Roitt, supra, Chapter 6.

Monospecific antiserum for use in immunological tests can be raised, e.g. in rabbits, against a purified lipolytic enzyme, e.g. as described in Chapter 41 of N. H. Axelsen, supra or Chapter 23 of N. H. Axelsen et al., A Manual of Quantitative Immunoelectrophoresis, Blackwell Scientific Publications (1973).

Production of lipolytic enzyme

The lipolytic enzyme of the invention may be produced by cultivation of one of the microorganisms described above in a suitable nutrient medium, containing carbon and nitrogen sources and inorganic salts, followed by recovery of the lipolytic enzyme.

After the cultivation, the lipolytic enzyme may be recovered and purified from the culture broth by conventional methods, such as hydrophobic chromatography, ion exchange chromatography and combinations thereof.

Convenient purification methods consist of an optional batch purification followed by two-step chromatography. The optional batch purification can be done by DEAE Streamline (product of Pharmacia), Super-Q Toyopearl, anion exchange resin or Macroprep HIC Support hydrophobic (product of Biorad). One part of the two-step chromatography may consist of hydrophobic chromatography, e.g. with Phenyl Toyopearl, Butyl Toyopearl or Macroprep HIC Support hydrophobic. The other part of the two-step chromatography may be done with an anion exchange resin, e.g. DEAE Toyopearl or Super-Q Toyopearl. The two steps may be carried in either sequence.

Application of lipolytic enzyme

The lipolytic enzyme of the invention may be used in conventional applications of lipolytic enzyme, particularly at a high pH, e.g. in laundry and dishwash detergents, in institutional and industrial cleaning and in leather processing.

The lipolytic enzymes of the invention can also be used for interesterification, for total hydrolysis of fats and oils and in optical isomer resolution processes.

Detergent additive

According to the invention, the lipolytic enzyme may typically be used as an additive in a detergent composition. This additive is conveniently formulated as a non-dusting granulate, a stabilized liquid, a slurry or a protected enzyme.

A suitable activity range for a detergent additive containing the lipolytic enzyme of this invention is 5,000–100,000 OPIDU/g (OPID measured at pH 9) or 0.01–100 mg pure enzyme protein per g of the additive.

Detergent

Advantageously, the lipolytic enzymes of this invention have high activity at alkaline pH (about pH 9–10), even in the absence of free $Ca^{++}$. This makes these lipolytic enzymes well suited for use in a wide range of detergents, even in detergents with a high content of builder to bind the free $Ca^{++}$.

The lipolytic enzyme of the invention may be incorporated in concentrations conventionally employed in detergents. The detergent composition of the invention may comprise lipolytic enzyme in an amount corresponding to 10–50,000 LU per gram of detergent, preferably 20–5,000 LU/g. The detergent may be dissolved in water to produce a wash liquor containing lipolytic enzyme in an amount corresponding to 25–15,000 LU per liter of wash liquor. The amount of lipolytic enzyme protein may be 0.001–10 mg per gram of detergent or 0.001–100 mg per liter of wash liquor.

Detergent composition

According to the invention, the lipolytic enzyme may typically be a component of a detergent composition. As such, it may be included in the detergent composition in the form of a non-dusting granulate, a stabilized liquid, or a protected enzyme. Non-dusting granulates may be produced, e.g., as disclosed in U.S. Pat. Nos. 4,106,991 and 4,661,452 (both to Novo Industri AS) and may optionally be coated by methods known in the art. Examples of waxy coating materials are poly(ethylene oxide) products (polyethylene glycol, PEG) with mean molecular weights of 1000 to 20000; ethoxylated nonylphenols having from 16 to 50 ethylene oxide units; ethoxylated fatty alcohols in which the alcohol contains from 12 to 20 carbon atoms and in which there are 15 to 80 ethylene oxide units; fatty alcohols; fatty acids; and mono- and di- and triglycerides of fatty acids. Examples of film-forming coating materials suitable for application by fluid bed techniques are given in patent GB 1483591. Liquid enzyme preparations may, for instance, be stabilized by adding a polyol such as propylene glycol, a sugar or sugar alcohol, lactic acid or boric acid according to established methods. Other enzyme stabilizers are well known in the art. Protected enzymes may be prepared according to the method disclosed in EP 238,216.

The detergent composition of the invention may be in any convenient form, e.g. as powder, granules, paste or liquid. A liquid detergent may be aqueous, typically containing up to 70% water and 0–30% organic solvent, or nonaqueous.

The detergent composition comprises one or more surfactants, each of which may be anionic, nonionic, cationic, or zwitterionic. The detergent will usually contain 0–50% of anionic surfactant such as linear alkylbenzene sulfonate (LAS), alpha-olefin sulfonate (AOS), alkyl sulfate (fatty alcohol sulfate) (AS), alcohol ethoxysulfate (AEOS or AES), secondary alkane sulfonates (SAS), alpha-sulfo fatty acid methyl esters, alkyl- or alkenylsuccinic acid, or soap. It may also contain 0–40% of nonionic surfactant such as alcohol ethoxylate (AEO or AE), carboxylated alcohol ethoxylates, nonylphenol ethoxylate, alkylpolyglycoside, alkyldimethylamine oxide, ethoxylated fatty acid monoethanolamide, fatty acid monoethanolamide, or polyhydroxy alkyl fatty acid amide (e.g. as described in WO 92/06154).

The detergent composition may additionally comprise one or more other enzymes, such as amylase, cutinase, protease, cellulase, peroxidase, and oxidase, e.g., laccase.

The detergent may contain 1–65% of a detergent builder or complexing agent such as zeolite, diphosphate, triphosphate, phosphonate, citrate, nitrilotriacetic acid (NTA), ethylenediaminetetraacetic acid (EDTA), diethylenetriaminepentaacetic acid (DTMPA), alkyl- or alkenylsuccinic acid, soluble silicates or layered silicates (e.g. SKS-6 from Hoechst). The detergent may also be unbuilt, i.e. essentially free of detergent builder.

The detergent may comprise one or more polymers. Examples are carboxymethyl cellulose (CMC), poly(vinyl pyrrolidone) (PVP), polyethylene glycol (PEG), poly(vinyl alcohol) (PVA), polycarboxylates such as polyacrylates, maleic/acrylic acid copolymers and lauryl methacrylate/acrylic acid copolymers.

The detergent may contain a bleaching system which may comprise a $H_2O_2$ source such as perborate or percarbonate which may be combined with a peracid-forming bleach activator such as tetraacetylethylenediamine (TAED) or nonanoyloxybenzene sulfonate (NOBS). Alternatively, the bleaching system may comprise peroxy acids of, e.g., the amide, imide, or sulfone type.

The enzymes of the detergent composition of the invention may be stabilized using conventional stabilizing agents, e.g. a polyol such as propylene glycol or glycerol, a sugar or sugar alcohol, lactic acid, boric acid, or a boric acid derivative such as, e.g., an aromatic borate ester, and the composition may be formulated as described in, e.g., WO 92/19709 and WO 92/19708.

The detergent may also contain other conventional detergent ingredients such as, e.g., fabric conditioners including clays, foam boosters, suds suppressors, anti-corrosion agents, soil-suspending agents, anti-soil-redeposition agents, dyes, bactericides, optical brighteners, or perfume.

The pH (measured in aqueous solution at use concentration) will usually be neutral or alkaline, e.g. in the range of 7–11.

Particular forms of detergent compositions within the scope of the invention include:

1) A detergent composition formulated as a granulate having a bulk density of at least 600 g/l comprising

| | |
|---|---|
| Linear alkylbenzene sulfonate (calculated as acid) | 7–12% |
| Alcohol ethoxysulfate (e.g. $C_{12-18}$ alcohol, 1-2 EO) or alkyl sulfate (e.g. $C_{16-18}$) | 1–4% |
| Alcohol ethoxylate (e.g. $C_{14-15}$ alcohol, 7 EO) | 5–9% |
| Sodium carbonate (as $Na_2CO_3$) | 14–20% |
| Soluble silicate (as $Na_2O_{,2}SiO_2$) | 2–6% |
| Zeolite (as $NaAlSiO_4$) | 15–22% |
| Sodium sulfate (as $Na_2SO_4$) | 0–6% |
| Sodium citrate/citric acid (as $C_6H_5Na_3O_7/C_6H_8O_7$) | 0–15% |
| Sodium perborate (as $NaBO_3.H_2O$) | 11–18% |
| TAED | 2–6% |
| Carboxymethyl cellulose | 0–2% |

-continued

| | |
|---|---|
| Polymers (e.g. maleic/acrylic acid copolymer, PVP PEG) | 0–3% |
| Enzymes (caculated as pure enzyme protein) | 0.0001–0.1% |
| Minor ingredients (e.g. suds suppressors, perfume, optical brightener, photobleach) | |
| Linear alkylbenzene sulfonate (calculated as acid) | 7–12% |
| | 0–5% |

2) A detergent composition formulated as a granulate having a bulk density of at least 600 g/l comprising

| | |
|---|---|
| Linear alkylbenzene sulfonate (calculated as acid) | 6–11% |
| Alcohol ethoxysulfate (e.g. $C_{12-8}$ alcohol, 1-2 EO or alkyl sulfate (e.g. $C_{16-18}$) | 1–3% |
| Alcohol ethoxylate (e.g. $C_{14-15}$ alcohol, 7 EO) | 5–9% |
| Sodium carbonate (as $Na_2CO_3$) | 15–21% |
| Soluble silicate (as $Na_2O$, $2SiO_2$) | 1–4% |
| Zeolite (as $NaAlSiO_4$) | 24–34% |
| Sodium sulfate (as $Na_2SO_4$) | 4–10% |
| Sodium citrate/citric acid (as $C_6H_5Na_3O_7/C_6H_8O_7$) | 0–15% |
| Carboxymethyl cellulose | 0–2% |
| Polymers (e.g. maleic/acrylic acid copolymer, PVP, PEG) | 1–6% |
| Enzymes (calculated as pure enzyme protein) | 0.0001–0.1% |
| Minor ingredients (e.g. suds suppressors, perfume) | 0–5% |

3) A detergent composition formulated as a granulate having a bulk density of at least 600 g/l comprising

| | |
|---|---|
| Linear alkylbenzene sulfonate (calculated as acid) | 5–9% |
| Alcohol ethoxylate (e.g. $C_{12-15}$ alcohol, 7 EO) | 7–14% |
| Soap as fatty acid (e.g. $C_{16-22}$ fatty acid) | 1–3% |
| Sodium carbonate (as $Na_2CO_3$) | 10–17% |
| Soluble silicate (as $Na_2O$, $2SiO_2$) | 3–9% |
| Zeolite (as $NaAlSiO_4$) | 23–33% |
| Sodium sulfate (as $Na_2SO4$) | 0–4% |
| Linear alkylbenzene sulfonate (calculated as acid) | 5–9% |
| Sodium perborate (as $NaBO_3.H_2O$) | 8–16% |
| TAED | 2–8% |
| Phosphonate (e.g. EDTMPA) | 0–1% |
| Carboxymethyl cellulose | 0–2% |
| Polymers (e.g. maleic/acrylic acid copolymer, PVP, PEG) | 0–3% |
| Enzymes (calculated as pure enzyme protein) | 0.0001–0.1% |
| Minor ingredients (e.g. suds suppressors, perfume, optical brightener) | 0–5% |

4) A detergent composition formulated as a granulate having a bulk density of at least 600 g/l comprising

| | |
|---|---|
| Linear alkylbenzene sulfonate (calculated as acid) | 8–12% |
| Alcohol ethoxylate (e.g. $C_{12-15}$ alcohol, 7 EO) | 10–25% |
| Sodium carbonate (as $Na_2CO_3$) | 14–22% |
| Soluble silicate (as $Na_2O$, $2SiO_2$) | 1–5% |
| Zeolite (as $NaAlSiO_4$) | 25–35% |
| Sodium sulfate (as $Na_2SO_4$) | 0–10% |
| Carboxymethyl cellulose | 0–2% |
| Polymers (e.g. maleic/acylic acid copolymer, PVP, PEG) | 1–3% |
| Enzymes (calculated as pure enzyme protein) | 0.0001–0.1% |
| Minor ingredients (e.g. suds suppressors, perfume) | 0–5% |

5) An aqueous liquid detergent composition comprising

| | |
|---|---|
| Linear alkylbenzene sulfonate (calculated as acid) | 15–21% |
| Alcohol ethoxylate (e.g. $C_{12-15}$ alcohol, 7 EO or $C_{12-15}$ alcohol, 5 EO) | 12–18% |
| Soap as fatty acid (e.g. oleic acid) | 3–13% |
| Alkenylsuccinic acid ($C_{12-14}$) | 0–13% |
| Aminoethanol | 8–18% |
| Citric acid | 2–8% |
| Linear alkylbenzene sulfonate (calculated as acid) | 15–21% |
| Phosphonate | 0–3% |

| | |
|---|---|
| Polymers (e.g. PVP, PEG) | 0–3% |
| Borate (as $B_4O_7$) | 0–2% |
| Ethanol | 0–3% |
| Propylene glycol | 8–14% |
| Enzymes (calculated as pure enzyme protein) | 0.0001–0.1% |
| Minor ingredients (e.g. dispersants suds suppressors perfume, optical brightener) | 0–5% |

6) An aqueous structured liquid detergent composition comprising

| | |
|---|---|
| Linear alkylbenzene sulfonate (calculated as acid) | 15–21% |
| Alcohol ethoxylate (e.g. $C_{12-15}$ alcohol, 7 EO, or $C_{12-15}$ alcohol, 5 EO) | 3–9% |
| Soap as fatty acid (e.g. oleic acid) | 3–10% |
| Zeolite (as $NaAlSiO_4$) | 14–22% |
| Potassium citrate | 9–18% |
| Borate (as $B_4O_7$) | 0–2% |
| Carboxymethyl cellulose | 0–2% |
| Polymers (e.g. PEG, PVP) | 0–3% |
| Anchoring polymers such as, e.g., lauryl methacrylate/acrylic acid copolymer; molar ratio 25:1; MW 3800 | 0–3% |
| Glycerol | 0–5% |
| Enzymes (calculated as pure enzyme protein) | 0.0001–0.1% |
| Minor ingredients (e.g. dispersants, suds suppressors, perfume, optical brighteners) | 0–5% |

7) A detergent composition formulated as a granulate having a bulk density of at least 600 g/l comprising

| | |
|---|---|
| Fatty alcohol sulfate | 5–10% |
| Ethoxylated fatty acid monoethanolamide | 3–9% |
| Soap as fatty acid | 0–3% |
| Sodium carbonate (as $Na_2CO_3$) | 5–10% |
| Soluble silicate (as $Na_2O$, $2SiO_2$) | 1–4% |
| Zeolite (as $NaAlSiO_4$) | 20–40% |
| Sodium sulfate (as $Na_2SO_4$) | 2–8% |
| Sodium perborate (as $NaBO_3.H_2O$) | 12–18% |
| TAED | 2–7% |
| Polymers (e.g. maleic/acrylic acid copolymer, PEG) | 1–5% |
| Enzymes (calculated as pure enzyme protein) | 0.0001–0.1% |
| Minor ingredients (e.g. optical brightener, suds suppressors, perfume) | 0–5% |

8) A detergent composition formulated as a granulate comprising

| | |
|---|---|
| Linear alkylbenzene sulfonate (calculated as acid) | 8–14% |
| Ethoxylated fatty acid monoethanolamide | 5–11% |
| Soap as fatty acid | 0–3% |
| Sodium carbonate (as $Na_2CO_3$) | 4–10% |
| Soluble silicate (as $Na_2O$, $2SiO_2$) | 1–4% |
| Zeolite (as $NaAlSiO_4$) | 30–50% |
| Sodium sulfate (as $Na_2SO_4$) | 3–11% |
| Sodium citrate (as $C_6H_5Na_3O_7$) | 5–12% |
| Polymers (e.g. PVP, maleic/acrylic acid copolymer, PEG) | 1–5% |
| Enzymes (calculated as pure enzyme protein) | 0.0001–0.1% |
| Minor ingredients (e.g. suds suppressors, perfume) | 0–5% |

9) A detergent composition formulated as a granulate comprising

| | |
|---|---|
| Linear alkylbenzene sulfonate (calculated as acid) | 6–12% |
| Nonionic surfactant | 1–4% |
| Soap as fatty acid | 2–6% |
| Sodium carbonate (as $Na_2CO_3$) | 14–22% |
| Zeolite (as $NaAlSiO_4$) | 18–32% |

-continued

| | |
|---|---|
| Sodium sulfate (as $Na_2SO_4$) | 5–20% |
| Sodium citrate (as $C_6H_5Na_3O_7$) | 3–8% |
| Sodium perborate (as $NaBO_3.H_2O$) | 4–9% |
| Bleach activator (e.g. NOBS or TAED) | 1–5% |
| Carboxymethyl cellulose | 0–2% |
| Polymers (e.g. polycarboxylate or PEG) | 1–5% |
| Enzymes (calculated as pure enzyme protein) | 0.0001–0.1% |
| Minor ingredients (e.g. optical brightener, perfume) | 0–5% |

10) An aqueous liquid detergent composition comprising

| | |
|---|---|
| Linear alkylbenzene sulfonate (calculated as acid) | 15–23% |
| Alcohol ethoxysulfate (e.g. $C_{12-15}$ alcohol, 2-3 EO) | 8–15% |
| Alcohol ethoxylate (e.g. $C_{12-15}$ alcohol, 7 EO, or $C_{12-15}$ alcohol, 3–9% 5 EO) | |
| Soap as fatty acid (e.g. lauric acid) | 0–3% |
| Aminoethanol | 1–5% |
| Sodium citrate | 5–10% |
| Hydrotrope (e.g. sodium toluene sulfonate) | 2–6% |
| Borate (as $B_4O_7$) | 0–2% |
| Carboxymethyl cellulose | 0–1% |
| Ethanol | 1–3% |
| Propylene glycol | 2–5% |
| Enzymes (calculated as pure enzyme protein) | 0.0001–0.1% |
| Minor ingredients (e.g. polymers, dispersants, perfume, optical brighteners) | 0–5% |

11) An aqueous liquid detergent composition comprising

| | |
|---|---|
| Linear alkylbenzene sulfonate (calculated as acid) | 20–32% |
| Alcohol ethoxylate (e.g. $C_{12-15}$ alcohol, 7 EO, or $C_{12-15}$ alcohol, 6–12% 5 EO) | |
| Aminoethanol | 2–6% |
| Citric acid | 8–14% |
| Borate (as $B_4O_7$) | 1–3% |
| Polymer (e.g. maleic/acrylic acid copolymer, anchoring polymer such as, e.g. lauryl methacrylate/acrylic acid copolymer) | 0–3% |
| Glycerol | 3–8% |
| Enzymes (calculated as pure enzyme protein) | 0.0001–0.1% |
| Minor ingredients (e.g. hydrotropes, dispersants, perfume, optical brighteners) | 0–5% |

12) A detergent composition formulated as a granulate having a bulk density of at least 600 g/l comprising

| | |
|---|---|
| Anionic surfactant (linear alkylbenzene sulfonate, alkyl sulfate, alpha-olefin sulfonate, alpha-sulfo fatty acid methyl esters, alkane sulfonates, soap) | 25–40% |
| Nonionic surfactant (e.g. alcohol ethoxylate) | 1–10% |
| Sodium carbonate (as $Na_2CO_3$) | 8–25% |
| Soluble silicates (as $Na_2O, 2SiO_2$) | 5–15% |
| Sodium sulfate (as $Na_2SO_4$) | 0–5% |
| Zeolite (as $NaAlSiO_4$) | 15–28% |
| Sodium perborate (as $NaBO_3.4H_2O$) | 0–20% |
| Bleach activator (TAED or NOBS) | 0–5% |
| Enzymes (calculated as pure enzyme protein) | 0.0001–0.1% |
| Minor ingredients (e.g. perfume, optical brighteners) | 0–3% |

13) Detergent formulations as described in 1)–12) wherein all or part of the linear alkylbenzene sulfonate is replaced by ($C_{12}$–$C_{18}$) alkyl sulfate.

14) A detergent composition formulated as a granulate having a bulk density of at least 600 g/l comprising

| | |
|---|---|
| ($C_{12}$–$C_{18}$) alkyl sulfate | 9–15% |
| Alcohol ethoxylate | 3–6% |
| Polyhydroxy alkyl fatty acid amide | 1–5% |
| Zeolite (as $NaAlSiO_4$) | 10–20% |
| Layered disilicate (e.g SK56 from Hoechst) | 10–20% |
| Sodium carbonate (as $Na_2CO_3$) | 3–12% |
| Soluble silicate (as $Na_2O, 2SiO_2$) | 0–6% |
| Sodium citrate | 4–8% |
| Sodium percarbonate | 13–22% |
| TAED | 3–8% |
| Polymers (e.g. polycarboxylates and PVP= | 0–5% |
| Enzymes (calculated as pure enzyme protein) | 0.0001–0.1% |
| Minor ingredients (e.g. optical brightener, photo bleach, perfume, suds suppressors) | 0–5% |

15) A detergent composition formulated as a granulate having a bulk density of at least 600 g/l comprising

| | |
|---|---|
| ($C_{12}$–$C_{18}$) alkyl sulfate | 4–8% |
| Alcohol ethoxylate | 11–15% |
| Soap | 1–4% |
| Zeolite MAP or zeolite A | 35–45% |
| Sodium carbonate (as $Na_2CO_3$) | 2–8% |
| Soluble silicate (as $Na_2O,2SiO_2$) | 0–4% |
| Sodium percarbonate | 13–22% |
| TAED | 1–8% |
| Carboxymethyl cellulose | 0–3% |
| Polymers (e.g. polycarboxylates and PVP) | 0–3% |
| Enzymes (calculated as pure enzyme protein) | 0.0001–0.1% |
| Minor ingredients (e.g. optical brightener, phosphonate, perfume) | 0–3% |

16) Detergent formulations as described in 1)–15) which contain a stabilized or encapsulated peracid, either as an additional component or as a substitute for already specified bleach systems.

17) Detergent compositions as described in 1), 3), 7), 9) and 12) wherein perborate is replaced by percarbonate.

18) Detergent compositions as described in 1), 3), 7), 9), 12), 14) and 15) which additionally contain a manganese catalyst. The manganese catalyst may, e.g., be one of the compounds described in "Efficient manganese catalysts for low-temperature bleaching", Nature 369, 1994, pp. 637–639.

19) Detergent composition formulated as a nonaqueous detergent liquid comprising a liquid nonionic surfactant such as, e.g., linear alkoxylated primary alcohol, a builder system (e.g. phosphate), enzyme and alkali. The detergent may also comprise anionic surfactant and/or a bleach system.

EXAMPLES

Culture media

The culture media shown in the table below were used in the examples.

| Ingredient | Composition of medium (g/L) | | | | | | | | | | | |
|---|---|---|---|---|---|---|---|---|---|---|---|---|
| | MR-10 | MT-O | OM | OM M | RS-G | YS-2 | YS-2SO | ToM a1 | ToM a5 | MT-O | ToM a10 | YPG |
| Pharmamedia | 10 | | | | 20 | | | | 30 | | 15 | |
| Soybean powder | 10 | 30 | | | 40 | | | 30 | | 30 | | |
| Yeast extract | | 1 | | | — | 10 | 10 | | | 1 | | 4 |
| Peptone | | 5 | | | — | 10 | 10 | | | 5 | | |
| Corn steep powder | | 5 | | | | | | | | 5 | | |
| Glucose | | 10 | | | — | 20 | 20 | | | 10 | | 15 |
| Sucrose | 2 | | | | | | | | | | 2.5 | |
| Glycerol | | | | | | | | 10 | | | | |
| Dried yeast | | | 30 | 30 | | | | | | | | |
| Oatmeal agar (Difco) | | | | 3 | | | | | | | | |
| Corn steep liquor | | | | | 10 | | | | | | | |
| Urea | | | | | 5<sup>x)</sup> | | | 1 | | | 0.5 | |
| Oatmeal agar (ISP No. 3 Difco) | | 3 | | | | | | | | | | |
| KH$_2$PO$_4$ | 5 | 4 | | | 1 | | 5 | 5 | 5 | 4 | 2.5 | 1 |
| MgSO$_4$.7H$_2$O | 0.2 | 0.2 | 0.2 | 0.5 | 0.5 | 1 | 1 | 1 | 0.4 | 0.1 | 0.5 | 0.5 |
| NH$_4$NO$_3$ | | 2.5 | | | | | | | | 2.5 | | |
| (NH$_4$)$_2$SO$_4$ | | | | | | | | 1.5 | | | | |
| Olive oil, ml/100 ml | 2 | 2 | 1 | | 2 | | | | | 2 | | |
| Soybean oil, ml/100 ml | | | | | | 2 | | | | | | |
| Jojoba oil ml/100 ml | | | | | | | | | 1 | | | |
| Soy lecithin, ml/100 ml | | | | | | | | | 2 | | | |
| Methyl oleate, ml/100 ml | | | | | | | | 2 | | | | |
| Sorbitan ester (Tween 40), ml/100 ml | | | | | | | | | | | 3 | |
| CaCO$_3$, tablets/100 ml | | | | | 2 | | | | | | | |
| pH adjusted to | 6.5 | — | 6.2 | 6.2 | 5.5 | 6.5 | 6.5 | 7.5 | 7.5 | 7 | 7.5 | 6.0 |

<sup>x)</sup>filtered separately

Example 1
Production of lipolytic enzyme from *A. corymbifera*

*A. corymbifera* strain NN100062 was cultivated for 3 days at 30° C. in shake flasks containing 100 ml of RS-G medium. 2,500 ml of cell-free broth was recovered from 50 shake flasks after removal of cell mass. This was freeze dried to obtain 58 g of powder sample with a lipolytic enzyme activity of 379 LU/g which was used in the following example.

Example 2
Washing effect of *A. corymbifera* lipolytic enzyme

The washing effect of lipolytic enzyme (powder preparation from the previous example) was evaluated by washing of soiled textile in detergent containing anionic surfactant (LAS) at pH 10. The test was done in a Terg-O-tometer laboratory washing machine at the following conditions:

| | |
|---|---|
| Temperature | 30° C. |
| Time | 30 minutes |
| Agitation | 100 rpm |
| Detergent | 0.25 g/l of LAS (linear alkylbenzene sulfonate, product name Nansa HS 80/S) + 1.0 g/l of Na$_2$CO$_3$ |
| Water | Tap water (approx. 18° German hardness) |
| pH | 10.0 |
| Lipolytic enzyme dosage | 2,000 LU/l |
| Test material | Cotton cloth, 7 × 7 cm, each stained with 85 mL of olive oil |
| Cloth/liquid ratio | 7 swatches/500 ml |

After washing, the swatches were Soxhlet extracted, and the residual amount of oil was determined gravimetrically. The composition of the residual oil was determined by TLC/FID analyses. A control experiment without lipolytic enzyme was made in the same manner. Results:

| | Without lipolytic enzyme | With lipolytic enzyme |
|---|---|---|
| Residual oil (mg) | 396 | 338 |
| Composition of residual oil: | | |
| % triglyceride | 92 | 32 |
| % free fatty acid | 4 | 53 |
| % 1,3-diglyceride | 2 | 9 |
| % 1,2-diglyceride | 2 | 5 |
| % monoglyceride | 0 | 0 |

It is seen that the lipolytic enzyme is effective in reducing the total amount residual oil and particularly reducing the amount of triglyceride in washing at pH 10:0 in the presence of LAS.

Example 3
Production and purification of lipolytic enzyme from *A. blakesleeana*

In this example, lipolytic enzyme activity was determined using olive oil emulsified with gum arabic. Conditions were 40° C., pH 10 (100 mM glycine buffer). 1 unit was taken as the amount of enzyme which liberates a titratable amount of fatty acid equivalent to 1 mmole of NaOH per minute.

*A. blakesleeana* strain NN100826 was cultivated for 3 days at 30° C. in shake flasks containing 100 ml of OM medium. The lipolytic enzyme yield was 41 units/ml.

Culture broth was collected from 50 shake flasks and concentrated to 2 L by ultrafiltration after washing with 2 L of deionized water. Ground ammonium sulfate was added to the concentrated broth under stirring in a cold chamber up to 40% saturation and left for 1 hour at 4° C. The precipitate was removed by centrifugation. Ammonium sulfate was further added to 50% saturation and the precipitate was removed. The supernatant was concentrated to 180 ml and dialyzed overnight using cellulose tube in 20 mM Tris/HCl buffer (pH 8.5) at 4° C. and freeze dried. 9.8 g of powder lipolytic enzyme preparation was obtained, having an activity of 1500 units/g.

Another powder lipolytic enzyme preparation was obtained by addition of chilled acetone to culture broth and freeze-drying of the precipitate.

Example 4
Washing effect of A. blakesleeana lipolytic enzyme

Powder lipolytic enzyme preparation from the previous example was tested in the same manner as the previous washing example with the following changes: The washing time was 20 minutes; each swatch of cloth was stained with 50 mL of oil; the swatches were aged for 2 days at room temperature before the washing test; and the pH, detergents and lipolytic enzyme dosages were as shown below. The analysis data were used to calculate the residual ester bonds (in mmoles) and the degree of hydrolysis.

| Detergent | pH | Lipolytic enzyme dosage (LU/l) | Residual oil (mg) | Residual ester bonds (mmoles) | DH (%) |
|---|---|---|---|---|---|
| 0.25 g/l LAS + | 9.5 | 0 | 185 | 607 | 3.2 |
| 0.25 g/l AE + | | 800 | 166 | 466 | 16.0 |
| 1.0 g/l Na$_2$CO$_3$ | | 2500 | 138 | 339 | 26.3 |
| 0.5 g/l LAS + | 9 | 0 | 171 | 556 | 4.1 |
| Na$_2$CO$_3$ | | 2500 | 158 | 496 | 7.1 |
| | 10 | 0 | 171 | 559 | 3.6 |
| | | 2500 | 153 | 462 | 10.4 |
| | 11 | 0 | 168 | 544 | 4.5 |
| | | 2500 | 162 | 509 | 6.7 |

It is seen that the lipolytic enzyme is effective in reducing the amount of residual oil and increasing the degree of hydrolysis, thus lowering the number of residual ester bonds.

Example 5
Production of lipolytic enzyme from A. blakesleeana

A. blakesleeana strain NN100826 was allowed to sporulate for 5 weeks on a slant of 39 g/l of PDA (product of Difco) and 10 g/l of agar in water.

9 ml of a 0.1% solution of Tween in water was poured onto the slant to make a spore suspension.

3 ml of the spore suspension was inoculated into a 500 ml baffled shake flask (two baffles) containing 100 ml of YS-2SO medium, and the flask was incubated with shaking (230 rpm) at 34° C. for 24 hours to prepare a seed culture.

The seed culture was homogenized to break up a pellet-shaped mycelium, and 2 ml of the homogenized culture was inoculated into a shake flask containing 100 ml of OMM medium and 2% of soybean lecithin. The flask was incubated with shaking (230 rpm) at 30° C. After 2 days cultivation, the broth had a lipolytic enzyme activity of 17.0 LU/ml and a pH of 6.7.

Example 6
Purification of lipolytic enzyme

Lipolytic enzyme from A. blakesleeana strain NN100826 was purified by three step chromatography, namely Streamline DEAE, Phenyl- and DEAE-Toyopearl, as follows.

Streamline DEAE column chromatography

Culture broth from 50 shake flasks prepared as in the previous example was centrifuged to obtain 2.8 L of a cell-free broth. This was applied onto 600 ml of Streamline DEAE pre-equilibrated with 50 mM sodium carbonate buffer, pH 10. Flow rate was 100 ml/min. After washing the column with the same buffer, bound lipolytic enzyme was eluted by 50 mM Tris buffer containing 0.6 M NaCl, pH 7.2. 38% and 36% of the starting lipolytic enzyme activity was recovered in the eluate and the pass-through fraction, respectively, i.e. a total recovery of 74%. For further purification the lipolytic enzyme bound to resin was used. The lipolytic enzyme solution was neutralized, then concentrated by UF module, 3000 NMWL. Recovery was 47%. After concentration the lipolytic enzyme was filtered through 0.2 mm membrane.

Phenyl Toyopearl column chromatography

It had been found that with gradient elution the lipolytic enzyme activity gave a very broad peak which was difficult to detect. Instead, step elution was used with 60 minutes of 1.4 M ammonium acetate, followed by 30 minutes of pure water and 30 minutes of 20% ethanol. The lipolytic enzyme activity gave two peaks. One was eluted by water ("lipolytic enzyme A") and the other eluted by 20% EtOH ("lipolytic enzyme B"). Recovery was 41% for lipolytic enzyme A and 33% for lipolytic enzyme B. Each lipolytic enzyme was concentrated and deionized by UF module, 3,000 NMWL. Recovery was 94% and 91%, respectively.

DEAE Toyopearl column chromatography

Lipolytic enzyme A was purified by gradient elution from 50 mM sodium carbonate buffer (pH 10) to 50 mM Tris buffer (pH 7.2)+0.6 M NaCl. Fractions with high lipolytic enzyme activity were pooled. The yield was 66%. The lipolytic enzyme was concentrated and deionized by UF module, 3,000 NMWL. Recovery was 69%.

SDS-PAGE showed the lipolytic enzyme to be pure with a single protein band. It was found to have isoelectric point at pH 8.0 and molecular weight 25,400. The specific activity of the pure lipolytic enzyme was found to be 3,300–4,100 LU/mg.

Lipolytic enzyme B was purified in a similar manner, and it was confirmed by SDS-PAGE that it was identical to lipolytic enzyme A.

Example 7
Production of lipolytic enzyme from various Absidia strains

Each of the Absidia strains shown in the table below was used for lipolytic enzyme production by the following steps.

Seed culture 2 days at 27° C. on YS-2 medium (omitted for NN100826).

Main culture

In shake flasks using the indicated medium at 27° C. (30° C. in one case, as noted). The cultivation time and lipolytic enzyme yield obtained are also shown in Table 2.

Recovery and purification

Centrifugation to get cell-free samples, followed by freeze-drying to make powder samples.

The culture conditions and the resulting yields are given below

| Species | Strain No. | Seed medium | Main medium | Days | Yield LU/ml |
|---|---|---|---|---|---|
| A. blakesleeana | NN000591 | YS-2 | MR-10 | 4 | 8.3 |
| A. blakesleeana | NN000987 | YS-2 | MT-O | 4 | 4.5 |
| A. blakesleeana | NN100826 | None | OMM + 2% lecithin | 2 (30° C.) | 17.0 |
| A. blakesleeana | NN102403 | YS-2 | MT-O | 4 | 3.0 |
| A. blakesleeana | NN102406 | YS-2 | OM | 4 | 3.2 |
| A. blakesleeana | NN102407 | YS-2 | MT-O | 4 | 2.6 |
| A. blakesleeana | NN102408 | YS-2 | MT-O | 4 | 4.9 |
| A. blakesleeana | NN102413 | YS-2 | MR-10 | 3 | 1.1 |
| A. corymbifera | NN100062 | YS-2 | MT-O | 5 | 32.0 |
| A. corymbifera | NN102404 | YS-2 | MT-O | 4 | 7.0 |
| A. corymbifera | NN102405 | YS-2 | MR-10 | 4 | 6.9 |
| A. corymbifera | NN100060 | YPG | ToMa1 | 5 | 45 |
| A. reflexa | NN102424 | YPG | ToMa1 | 5 | 16 |
| A. blakesleeana | NN102407 | YS-2 | ToMa5 | 5 | 40 |
| A. blakesleeana | NN102408 | YS-2 | ToMa5 | 6 | 25 |
| A. blakesleeana | NN000987 | YPG | ToMa1 | 5 | 30 |
| A. blakesleeana | NN102413 | YPG | ToMa1 | 6 | 20 |
| A. blakesleeana var. atrospora | NN102423 | YS-2 | ToMa5 | 6 | 20 |
| A. corymbifera | NN102426 | YPG | ToMa1 | 5 | 22 |
| A. sporophora-variabilis | NN102427 | YS-2 | ToMa1 | 4 | 20 |
| A. blakesleeana | NN102432 | YS-2 | ToMa5 | 5 | 15 |
| A. blakesleeana | NN100826 | YS-2 | ToMa5 | 5 | 40 |
| A. corymbifera | NN100062 | YPG | ToMa1 | 5 | 70 |
| A. blakesleeana | NN000591 | YPG | ToMa1 | 5 | 70 |
| A. blakesleeana | NN102403 | YPG | ToMa1 | 5 | 40 |
| A. corymbifera | NN102404 | YPG | ToMa1 | 4 | 30 |
| A. corymbifera | NN102405 | YS-2 | ToMa1 | 5 | 30 |
| A. blakesleeana | NN102406 | YS-2 | ToMa5 | 6 | 30 |
| A. cylindrospora var rhizomorpha | NN102422 | YPG | ToMa10 | 5 | 3.2 (pH 9) |
| A. pseudo-cylindrospora | NN102434 | YS-2 | MT-O | 5 | 0–1 |

Example 8
Effect of pH and $Ca^{++}$ on activity of Absidia lipolytic enzymes

The lipolytic enzyme activity was tested in the range pH 7–10 without $Ca^{++}$ by the OPID method described above, using a lipolytic enzyme amount of 20 LU/ml. Purified lipolytic enzymes according to the invention from the following strains were tested:

A. blakesleeana NN000591

A. blakesleeana NN000987

A. blakesleeana NN100826

A. corymbifera NN100062

A. reflexa NN102424

The results are shown in the enclosed figures.

It is seen that in the absence of $Ca^{++}$, all the Absidia lipolytic enzymes tested show higher activity at pH 9 than pH 8 (optimum at about pH 9 or higher), and the lipolytic enzyme from A. reflexa shows higher activity at pH 10 than pH 9 (optimum at about pH 10 or higher). It is also seen that the lipolytic enzymes from Absidia subgenus Mycocladus (represented by A. blakesleeana and A. corymbifera) show an activity at pH 9 in the absence of $Ca^{++}$ above 3 OPIDU/ml for a lipolytic enzyme dosage of 20 LU/ml, i.e. a ratio of above 0.15 OPIDU/LU.

Example 9
Plate test for lipolytic enzyme activity at pH 10

The plate test described in Example 11 of WO 88/02775 (corresponding to JP-W 1-501120) was used to check for lipolytic enzyme activity at pH 10 with and without the addition of $Ca^{++}$. Lipolytic enzyme preparations from all the strains listed in Example 7 were found to exhibit lipolytic enzyme activity at pH 10, both with and without $Ca^{++}$ addition:

Example 10
pI and MW of lipolytic enzymes

Purified lipolytic enzymes from some strains were used to determine the iso-electric point (pI) by preparative iso-electric focusing and the molecular weight (MW) by SDS-PAGE. Results:

| Species | Strain No. | pI | MW |
|---|---|---|---|
| A. blakesleeana | NN100826 | 8 | 25 kDa |
| A. corymbifera | NN100062 | 5.2–5.8 | 32 kDa (SDS) |
| A. blakesleeana | NN000987 | 6.5 | 30 kDa |
| A. blakesleeana | NN000591 | 6.5 | 30 kDa |
| A. reflexa | NN102424 | 4.1 | — |
| A. sporophoro-variabilis | NN102427 | 3.6–5 | — |

A separate purification of the lipase from A. blakesleeana NN100826 suggests the size to be 31–32 KDa. The 25 KDa lipase therefore probably represents a slightly truncated lipase molecule.

Example 11
Structural characterization of A. blakesleeana lipolytic enzymes

The N-terminal sequences of lipolytic enzymes from A. blakesleeana NN000591 and NN000987 were determined following electroblotting. Both lipolytic enzymes have a molecular weight of around 30 kDa.

The N-terminal acid sequencing of the lipolytic enzyme from NN000987 gave the sequence shown as SEQ ID NO: 1 in the enclosed sequence listing.

The N-terminal sequencing of the lipolytic enzyme from NN000591 gave two sequences shown as SEQ ID NO: 2 and SEQ ID NO: 3.

It is seen that for NN000591, the N-terminal sequence shown as SEQ ID NO: 3 starts at amino acid residue 6 of the N-terminal sequence shown as SEQ ID NO: 2. Thus, the two sequences represent variable processing of the same protein either during synthesis or purification. In addition, it is clear that SEQ ID NO: 1 for NN000987 and SEQ ID NO: 2 for NN000591 represent the same N-terminal sequence, and it is believed that the two lipolytic enzymes are most likely identical. Thus, based on the 3 above N-terminal sequences, it is concluded that the mature lipolytic enzyme has the N-terminal sequence shown as SEQ ID NO: 4.

In addition to the 30 kDa lipolytic enzyme in the NN000591 preparation, a band with molecular weight around 21 kDa was seen. N-terminal amino acid sequencing of this protein following electroblotting gave the sequence shown as SEQ ID NO: 5. This N-terminal sequence could be aligned to the lid of the known sequence for the lipase from *Rhizomucor miehei*, so it was concluded that it is a fragment of the full-length 30 kDa lipolytic enzyme.

The NN000591 lipolytic enzyme was reduced and S-carboxymethylated before degradation with a lysyl-specific protease. The resulting peptides were fractionated and re-purified using reversed phase HPLC before being subjected to N-terminal amino acid sequencing. The peptide sequences shown as SEQ ID NO: 6–10 were obtained.

By aligning the sequences with the known sequences of the lipases from *Rhizomucor miehei* and *Rhizopus delemar*, it was concluded that the full-length lipolytic enzyme contains the sequences SEQ ID NO: 4–10 in this order. In these sequences, Xaa represents an amino acid that could not be identified. Asx designates positions where Asp and Asn could not be distinguished. The amino acids in positions 1 and 9 of SEQ ID NO: 5 are uncertain.

Example 12

Purification of *A. corymbifera* lipolytic enzyme

Lipolytic enzyme from *A. corymbifera* strain NN100062 was purified as follows.

Streamline

Crude lipolytic enzyme powder obtained by cultivation of the strain was dissolved in 50 mM sodium carbonate buffer (pH 10). After centrifugation, lipolytic enzyme sample was adsorbed on expanded DEAE resin equilibrated with the same buffer, and then the resin was washed with the same buffer. The lipolytic enzyme was eluted with Tris-HCl buffer (pH 7.6) containing 0.5 M NaCl. The yield of this step was 52%.

Butyl Toyopearl

The second step was hydrophobic column chromatography using pre-packed Butyl Toyopearl and HPLC. The concentrated lipolytic enzyme was adjusted to a salt concentration of 1 M ammonium acetate and then adsorbed on a column equilibrated with 1 M ammonium acetate. Elution was carried out with a linear gradient of 1–0 M ammonium acetate and 20% ethanol. The lipolytic enzyme activity of each fraction was measured, and the fractions with high lipolytic enzyme activity were gathered and desalted with micro asilizer (product of Asahi Kasei).

DEAE Toyopearl column chromatography

The third step was anion column chromatography using pre-packed DEAE Toyopearl and HPLC (product of Waters). The lipolytic enzyme was adjusted to pH 8.5. This was applied to a column equilibrated with 50 mM Tris-HCl buffer (pH 8.5), and the lipolytic enzyme was eluted with a linear gradient of 0–0.5 M NaCl. The fractions with high lipolytic enzyme activity were gathered, and the obtained lipolytic enzyme was concentrated. The yield of this step was 66%.

Gel filtration

The final step was gel filtration. The buffer used was 50 mM Tris-HCl containing 0.15 M NaCl. Again, the fractions with high lipolytic enzyme activity were gathered.

The purification is summarized in the following table.

| Step | Activity (LU) | Specific activity (LU/mg) | Yield (%) |
| --- | --- | --- | --- |
| Powder | 135500 | 18 | 100 |
| STREAM LINE | 69840 | 18 | 52 |
| Butyl Toyopearl | 28210 | 215 | 21 |
| DEAE Toyopearl | 15500 | 4250 | 8.5 |
| Gel filtration | 10140 | 5200 | 7.5 |

Example 13

Structural characterization of *A. corymbifera* lipolytic enzyme

The structure of the lipolytic enzyme of *A. corymbifera* NN100062 was studied in the same manner as in Example 11. The N-terminal sequencing gave the sequence shown as SEQ ID NO: 11. Peptides obtained after degradation were found to have the sequences shown as SEQ ID NO: 12–16 and 18–19. It was found that the residue Asn20 of SEQ ID NO: 12 was glycosylated.

A comparison showed that 22 amino acids at the C-terminal of SEQ ID NO: 15 are identical to those at the N-terminal of SEQ ID NO: 16, and it was concluded that these two sequences form part of a larger fragment shown as SEQ ID NO: 17. By alignment with the known sequences of the lipases from *Rhizomucor miehei* and *Rhizopus delemar*, it was concluded that the full-length lipolytic enzyme contains the sequences SEQ ID NO: 11–14 and 17–19 in this order.

Example 14

Substrate affinity of lipolytic enzyme from *A. sporophora-variabilis*

The following procedure was used for a simple determination of the ability of a lipolytic enzyme to accumulate on/in a substrate phase (olive oil) at alkaline pH (pH 9.0) in the presence of non-ionic surfactant Dobanol 25-7 (2500 ppm).

Two identical solutions of the lipolytic enzyme in buffer with non-ionic surfactant were prepared in sealable vials, and substrate was added to one of the solutions. Both solutions were incubated with vigorous shaking, and the remaining lipolytic enzyme activity was determined (in LU, defined above) after separation and removal of the substrate.

The following conditions were used:

| | |
| --- | --- |
| Buffer: | 100 mM Glycine (pH 9.0) |
| Non-ionic surfactant | 100 ppm alcohol ethoxylate (Dobanol ™ 25-7) |
| Substrate: | Olive oil |
| Buffer:substrate | 50:50 v/v |
| Incubation temperature | 4° C. |
| Initial lipolytic enzyme activity | 5–10 LU/ml |
| Incubation time | Over night (24–26 hours). |

Lipolase® (a commercially available fungal lipolytic enzyme) was used for comparison. The results are given as the residual activity after incubation with substrate relative to the activity without substrate.

| | |
|---|---|
| Lipolase ® | 94% |
| *A. sporophora-variabilis* lipolytic enzyme | 39% |

The results show that whereas Lipolase tends to remain totally in the aqueous phase under the conditions employed, the lipolytic enzyme from *A. sporophora-variabilis* has a higher affinity for olive oil, leaving less than 50% of the added activity in the aqueous phase after overnight incubation.

We claim:

1. An enzymatic detergent composition comprising a surfactant and 10–50,000 LU/g of detergent alkaline Absidia lipolytic enzyme selected from the group consisting of *A. blakesleeana, A. corymbifera, A. cylindrospora* var. *rhizomorpha, A. pseudocylindrospora, A. reflexa*, and mixtures thereof, wherein the lipolytic enzyme has a higher lipolytic enzyme activity at pH 9 than at pH 8 in the absence of free $Ca^{++}$.

2. The detergent composition of claim 1 wherein the lipolytic enzyme exhibits a pH optimum at about pH 9.0 or above as measured at 30° C.

3. The detergent composition of claim 1, wherein the Absidia strain is *A. blakesleeana*.

4. The detergent composition of claim 1, wherein the Absidia strain is *A. blakesleeana* var. *atrospora*.

5. The detergent composition of claim 1, wherein the Absidia strain is *A. corymbifera*.

6. The detergent composition of claim 1 wherein the lipolytic enzyme is derived from a strain of Absidia Subgenus Absidia Group B.

7. The detergent composition of claim 6 wherein the Absidia strain is *A. cylindrospora* var. *rhizomorpha* or *A. pseudocylindrospora*.

8. The detergent composition of claim 1 wherein the lipolytic enzyme is derived from a strain of *A. reflexa* and wherein the lipolytic enzyme exhibits a higher lipolytic enzyme activity at pH 10 than pH 9 in the absence of free $Ca^{++}$.

9. The detergent composition of claim 1 wherein the lipolytic enzyme comprises an amino acid sequence selected from the group consisting of SEQ ID NO: 4, 5, 6, 7, 8, 9 and 10.

10. The detergent composition of claim 9, wherein the lipolytic enzyme comprises two or more of said sequences.

11. The detergent composition of claim 1 wherein the lipolytic enzyme comprises an amino acid sequence selected from the group consisting of SEQ ID NO: 11, 12, 13, 14, 17, 18 and 19.

12. The detergent composition of claim 11 wherein the lipolytic enzyme comprises two or more of said sequences.

13. The detergent composition of claim 11, further comprising 5–40% by weight of a detergent builder, wherein the composition has a pH of 8–10.5 measured in an aqueous solution.

14. A method for removing fatty soiling from textile, comprising washing the textile in an aqueous solution comprising the detergent composition of claim 1.

15. The method of claim 14 wherein the aqueous solution comprises essentially no free $Ca^{++}$ ions or contains free $Ca^{++}$ ions in an amount below 1 mM.

16. An enzymatic detergent additive in the form of a non-dusting granulate, a stabilized liquid, a slurry, or a protected enzyme, wherein the additive comprises a surfactant and an alkaline Absidia lipolytic enzyme in an amount of 10 to 50,000 LU/g detergent selected from the group consisting of *A. blakesleeana, A. corymbifera, A. cylindrospora* var. *rhizomorpha, A. pseudocylindrospora, A. reflexa* and mixtures thereof, and wherein the lipolytic enzyme exhibits a higher lipolytic enzyme activity at pH 9 than pH 8 in the absence of free $Ca^{++}$.

17. The enzymatic detergent additive of claim 16 wherein the lipolytic enzyme exhibits a pH optimum at about pH 9.0 or above as measured at 30° C.

18. The enzymatic detergent additive of claim 16 wherein the Absidia strain is *A. blakesleeana*.

19. The enzymatic detergent additive of claim 16 wherein the Absidia strain is *A. blakesleeana* var. *atrospora*.

20. The enzymatic detergent additive of claim 16 wherein the Absidia strain is *A. corymbifera*.

21. The enzymatic detergent additive of claim 16 wherein the Absidia strain is *A. cylindrospora* var. *rhizomorpha* or *A. pseudocylindrospora*.

22. The enzymatic detergent additive of claim 16 wherein the lipolytic enzyme is derived from a strain of *A. reflexa* and exhibits a higher lipolytic enzyme activity at pH 10 than pH 9 in the absence of free $Ca^{++}$.

23. The enzymatic detergent additive of claim 16 wherein the lipolytic enzyme comprises an amino acid sequence selected from the group consisting of SEQ ID NO: 4, 5, 6, 7, 8, 9 and 10.

24. The enzymatic detergent additive of claim 23 wherein the lipolytic enzyme comprises two or more of said sequences.

25. The enzymatic detergent additive of claim 16 wherein the lipolytic enzyme comprises an amino acid sequence selected from the group consisting of SEQ ID NO: 11, 12, 13, 14, 17, 18 and 19.

26. The enzymatic detergent additive of claim 25 wherein the lipolytic enzyme comprises two or more of said sequences.

27. The detergent composition of claim 10, wherein the lipolytic enzyme comprises SEQ ID NO: 4, 5, 6, 7, 8, 9 and 10.

28. The detergent composition of claim 12, wherein the lipolytic enzyme comprises SEQ ID NO: 4, 5, 6, 7, 8, 9 and 10.

29. The method of claim 15 wherein the free $Ca^{++}$ ions in an amount below 0.2 mM.

30. The enzymatic detergent additive of claim 24, wherein the lipolytic enzyme comprises SEQ ID NO: 4, 5, 6, 7, 8, 9 and 10.

31. The enzymatic detergent additive of claim 26, wherein the lipolytic enzyme comprises SEQ ID NO: 4, 5, 6, 7, 8, 9 and 10.

* * * * *

```
                        SEQUENCE LISTING (1) GENERAL INFORMATION:

(iii) NUMBER OF SEQUENCES: 19

(2) INFORMATION FOR SEQ ID NO:1:

(i) SEQUENCE CHARACTERISTICS:
         (A) LENGTH: 19 amino acids
         (B) TYPE: amino acid
         (C) STRANDEDNESS: single
         (D) TOPOLOGY: linear (ii) MOLECULE TYPE: None (xi) SEQUENCE DESCRIPTION: SEQ ID NO:1:

Ser Ser Xaa Lys Gln Asx Tyr Arg Thr Ala Ser Glu Thr Glu Ile Gln
1               5                  10                  15

Ala His Thr (2) INFORMATION FOR SEQ ID NO:2:

(i) SEQUENCE CHARACTERISTICS:
         (A) LENGTH: 16 amino acids
         (B) TYPE: amino acid
         (C) STRANDEDNESS: single
         (D) TOPOLOGY: linear (ii) MOLECULE TYPE: None (xi) SEQUENCE DESCRIPTION: SEQ ID NO:2:

Ser Ser Xaa Xaa Gln Asx Tyr Arg Thr Ala Ser Glu Thr Glu Ile Gln
1               5                  10                  15

(2) INFORMATION FOR SEQ ID NO:3:

(i) SEQUENCE CHARACTERISTICS:
         (A) LENGTH: 16 amino acids
         (B) TYPE: amino acid
         (C) STRANDEDNESS: single
         (D) TOPOLOGY: linear (ii) MOLECULE TYPE: None (xi) SEQUENCE DESCRIPTION: SEQ ID NO:3:

Asx Tyr Arg Thr Ala Ser Glu Thr Glu Ile Gln Ala His Thr Phe Tyr
1               5                  10                  15

(2) INFORMATION FOR SEQ ID NO:4:

(i) SEQUENCE CHARACTERISTICS:
         (A) LENGTH: 21 amino acids
         (B) TYPE: amino acid
         (C) STRANDEDNESS: single
         (D) TOPOLOGY: linear (ii) MOLECULE TYPE: None (xi) SEQUENCE DESCRIPTION: SEQ ID NO:4:
```

```
Ser Ser Xaa Lys Gln Asx Tyr Arg Thr Ala Ser Glu Thr Glu Ile Gln
1               5                   10                  15
Ala His Thr Phe Tyr
            20
```

(2) INFORMATION FOR SEQ ID NO:5:

(i) SEQUENCE CHARACTERISTICS:
        (A) LENGTH: 13 amino acids
        (B) TYPE: amino acid
        (C) STRANDEDNESS: single
        (D) TOPOLOGY: linear (ii) MOLECULE TYPE: None (xi) SEQUENCE DESCRIPTION: SEQ ID NO:5:

```
Ile Ala Asn Ile Val Phe Val Pro Val Asx Tyr Pro Pro
1               5                   10
```

(2) INFORMATION FOR SEQ ID NO:6:

(i) SEQUENCE CHARACTERISTICS:
        (A) LENGTH: 18 amino acids
        (B) TYPE: amino acid
        (C) STRANDEDNESS: single
        (D) TOPOLOGY: linear (ii) MOLECULE TYPE: None (xi) SEQUENCE DESCRIPTION: SEQ ID NO:6:

```
Gly Phe Leu Asx Ser Tyr Asx Glu Val Gln Asx Gln Leu Val Ala Glu
1               5                   10                  15
Val Lys
```

(2) INFORMATION FOR SEQ ID NO:7:

(i) SEQUENCE CHARACTERISTICS:
        (A) LENGTH: 18 amino acids
        (B) TYPE: amino acid
        (C) STRANDEDNESS: single
        (D) TOPOLOGY: linear (ii) MOLECULE TYPE: None (xi) SEQUENCE DESCRIPTION: SEQ ID NO:7:

```
Ile Val Val Ala Gly His Ser Leu Gly Gly Ala Thr Ala Val Leu Xaa
1               5                   10                  15
Ala Leu
```

(2) INFORMATION FOR SEQ ID NO:8:

(i) SEQUENCE CHARACTERISTICS:
        (A) LENGTH: 27 amino acids
        (B) TYPE: amino acid
        (C) STRANDEDNESS: single
        (D) TOPOLOGY: linear (ii) MOLECULE TYPE: None (xi) SEQUENCE DESCRIPTION: SEQ ID NO:8:

```
Ile Pro Tyr Gln Arg Leu Val Asn Glu Arg Asp Ile Val Pro His Leu
1               5                   10                  15
Pro Pro Gly Ala Phe Gly Phe Leu Xaa Ala Gly
            20                  25
```

(2) INFORMATION FOR SEQ ID NO:9:

```
    (i) SEQUENCE CHARACTERISTICS:
        (A) LENGTH: 23 amino acids
        (B) TYPE: amino acid
        (C) STRANDEDNESS: single
        (D) TOPOLOGY: linear (ii) MOLECULE TYPE: None (xi) SEQUENCE DESCRIPTION: SEQ ID NO:9:

Asp Ser Ser Leu Arg Val Cys Pro Asn Gly Ile Glu Thr Asp Asp Cys
 1               5                  10                  15

Ser Asn Ser Ile Val Pro Phe
             20

(2) INFORMATION FOR SEQ ID NO:10:

(i) SEQUENCE CHARACTERISTICS:
        (A) LENGTH: 6 amino acids
        (B) TYPE: amino acid
        (C) STRANDEDNESS: single
        (D) TOPOLOGY: linear (ii) MOLECULE TYPE: None (xi) SEQUENCE DESCRIPTION: SEQ ID NO:10:

Thr Ser Val Ile Asp His
 1               5

(2) INFORMATION FOR SEQ ID NO:11:

(i) SEQUENCE CHARACTERISTICS:
        (A) LENGTH: 25 amino acids
        (B) TYPE: amino acid
        (C) STRANDEDNESS: single
        (D) TOPOLOGY: linear (ii) MOLECULE TYPE: None (xi) SEQUENCE DESCRIPTION: SEQ ID NO:11:

Ser Thr Gln Asp Tyr Arg Ile Ala Ser Glu Ala Glu Ile Lys Ala His
 1               5                  10                  15

Thr Phe Tyr Thr Ala Leu Ser Ala Asn
             20                  25

(2) INFORMATION FOR SEQ ID NO:12:

(i) SEQUENCE CHARACTERISTICS:
        (A) LENGTH: 23 amino acids
        (B) TYPE: amino acid
        (C) STRANDEDNESS: single
        (D) TOPOLOGY: linear (ii) MOLECULE TYPE: None (xi) SEQUENCE DESCRIPTION: SEQ ID NO:12:

Thr Val Ile Pro Gly Gly Gln Trp Ser Cys Pro His Cys Asp Val Ala
 1               5                  10                  15

Pro Asn Leu Asn Ile Thr Lys
             20

(2) INFORMATION FOR SEQ ID NO:13:

(i) SEQUENCE CHARACTERISTICS:
        (A) LENGTH: 12 amino acids
        (B) TYPE: amino acid
        (C) STRANDEDNESS: single
        (D) TOPOLOGY: linear (ii) MOLECULE TYPE: None
```

(xi) SEQUENCE DESCRIPTION: SEQ ID NO:13:

Gly Phe Leu Asp Ser Tyr Asn Glu Val Gln Asp Lys
1               5                   10

(2) INFORMATION FOR SEQ ID NO:14:

(i) SEQUENCE CHARACTERISTICS:
        (A) LENGTH: 10 amino acids
        (B) TYPE: amino acid
        (C) STRANDEDNESS: single
        (D) TOPOLOGY: linear (ii) MOLECULE TYPE: None (xi) SEQUENCE DESCRIPTION: SEQ ID NO:14:

Ala Gln Leu Asp Arg His Pro Gly Tyr Lys
1               5                   10

(2) INFORMATION FOR SEQ ID NO:15:

(i) SEQUENCE CHARACTERISTICS:
        (A) LENGTH: 38 amino acids
        (B) TYPE: amino acid
        (C) STRANDEDNESS: single
        (D) TOPOLOGY: linear (ii) MOLECULE TYPE: None (xi) SEQUENCE DESCRIPTION: SEQ ID NO:15:

Ile Val Val Thr Gly His Ser Leu Gly Gly Ala Thr Ala Val Leu Ser
1               5                   10                  15
Ala Leu Asp Leu Tyr His His Gly His Asp Asn Ile Glu Ile Tyr Thr
                20                  25                  30
Gln Gly Gln Pro Arg Ile
        35

(2) INFORMATION FOR SEQ ID NO:16:

(i) SEQUENCE CHARACTERISTICS:
        (A) LENGTH: 31 amino acids
        (B) TYPE: amino acid
        (C) STRANDEDNESS: single
        (D) TOPOLOGY: linear (ii) MOLECULE TYPE: None (xi) SEQUENCE DESCRIPTION: SEQ ID NO:16:

Ala Leu Asp Leu Tyr His His Gly His Asp Asn Ile Glu Ile Tyr Thr
1               5                   10                  15
Gln Gly Gln Pro Arg Ile Gly Gly Pro Glu Phe Ala Asn Tyr Val
                20                  25                  30

(2) INFORMATION FOR SEQ ID NO:17:

(i) SEQUENCE CHARACTERISTICS:
        (A) LENGTH: 47 amino acids
        (B) TYPE: amino acid
        (C) STRANDEDNESS: single
        (D) TOPOLOGY: linear (ii) MOLECULE TYPE: None (xi) SEQUENCE DESCRIPTION: SEQ ID NO:17:

Ile Val Val Thr Gly His Ser Leu Gly Gly Ala Thr Ala Val Leu Ser
1               5                   10                  15

```
Ala Leu Asp Leu Tyr His His Gly His Asp Asn Ile Glu Ile Tyr Thr
            20              25              30

Gln Gly Gln Pro Arg Ile Gly Gly Pro Glu Phe Ala Asn Tyr Val
            35              40              45
```

(2) INFORMATION FOR SEQ ID NO:18:

(i) SEQUENCE CHARACTERISTICS:
        (A) LENGTH: 34 amino acids
        (B) TYPE: amino acid
        (C) STRANDEDNESS: single
        (D) TOPOLOGY: linear (ii) MOLECULE TYPE: None (xi) SEQUENCE DESCRIPTION: SEQ ID NO:18:

```
Ile Pro Tyr Gln Arg Leu Val Asn Glu Arg Asp Ile Val Pro His Leu
 1               5                  10                  15

Pro Pro Gly Ala Phe Gly Phe Leu His Ala Gly Glu Glu Phe Trp Ile
            20              25              30

Met Lys
```

(2) INFORMATION FOR SEQ ID NO:19:

(i) SEQUENCE CHARACTERISTICS:
        (A) LENGTH: 23 amino acids
        (B) TYPE: amino acid
        (C) STRANDEDNESS: single
        (D) TOPOLOGY: linear (ii) MOLECULE TYPE: None (xi) SEQUENCE DESCRIPTION: SEQ ID NO:19:

```
Asp Ser Ser Leu Arg Val Cys Pro Asn Gly Ile Glu Thr Asp Asn Cys
 1               5                  10                  15

Ser Asn Ser Ile Val Pro Phe
            20
```